(12) United States Patent
Ohba et al.

(10) Patent No.: US 10,815,263 B2
(45) Date of Patent: Oct. 27, 2020

(54) METHOD FOR PURIFYING P1,P4-DI(URIDINE 5'-)TETRAPHOSPHATE

(71) Applicant: YAMASA CORPORATION, Choshi-shi (JP)

(72) Inventors: Yusuke Ohba, Choshi (JP); Tomoko Oyama, Choshi (JP); Fumitaka Kano, Choshi (JP); Asuka Uchino, Choshi (JP)

(73) Assignee: YAMASA CORPORATION, Choshi-shi (JP)

( * ) Notice: Subject to any disclaimer, the term of this patent is extended or adjusted under 35 U.S.C. 154(b) by 21 days.

(21) Appl. No.: 16/339,485

(22) PCT Filed: Oct. 24, 2017

(86) PCT No.: PCT/JP2017/038237
§ 371 (c)(1),
(2) Date: Apr. 4, 2019

(87) PCT Pub. No.: WO2018/079503
PCT Pub. Date: May 3, 2018

(65) Prior Publication Data
US 2019/0233462 A1    Aug. 1, 2019

(30) Foreign Application Priority Data

Oct. 25, 2016 (JP) ................................ 2016-209024
Oct. 25, 2016 (JP) ................................ 2016-209026

(51) Int. Cl.
*A61K 31/7105* (2006.01)
*A61P 27/02* (2006.01)
*C07H 19/10* (2006.01)
*C07H 1/06* (2006.01)

(52) U.S. Cl.
CPC .......... *C07H 19/10* (2013.01); *A61K 31/7105* (2013.01); *A61P 27/02* (2018.01); *C07H 1/06* (2013.01)

(58) Field of Classification Search
None
See application file for complete search history.

(56) References Cited

U.S. PATENT DOCUMENTS

| 6,458,946 B1 | 10/2002 | Maeda et al. |
| 2002/0156269 A1 | 10/2002 | Maeda et al. |
| 2010/0016567 A1 | 1/2010 | Kogo et al. |
| 2016/0194347 A1 | 7/2016 | Yamada |

FOREIGN PATENT DOCUMENTS

| WO | WO 2000/20430 A1 | 4/2000 |
| WO | WO 2008/012949 A1 | 1/2008 |
| WO | WO 2008/024169 A1 | 2/2008 |
| WO | WO 2014/103704 A1 | 7/2014 |

OTHER PUBLICATIONS

International Search Report dated Jan. 9, 2018 in PCT/JP2017/038237 filed on Oct. 24, 2017.
William Pendergast, et al., "Synthesis and P2Y Receptor Activity of a Series of Uridine Dinucleoside 5'-Polyphosphates," Bioorganic & Medicinal Chemistry Letters, vol. 11, pp. 157-160, 2001.
Ivan B. Yanachkov, "$P^1,P^2$-Diimidazolyl Derivatives of Pyrophosphate and Bis-Phosphonates—Synthesis, Properties, and Use in Preparation of Dinucleoside Tetraphosphates and Analogs", Organic & Biomolecular Chemistry, vol. 9; pp. 730-738, 2011.
Hiroshi Nishino, SSOC Journal, vol. 40, No. 9, pp. 853-854, DOI: 10.5059/yukigoseikyokaishi.40.853, 1982.
Hiroyuki Aoki, et al., "Industrial Production and Market of Activated Carbon", TANSO, 232, pp. 98-107, DOI:10.7209/tanso.2008.98, 2008.

*Primary Examiner* — Layla D Berry
(74) *Attorney, Agent, or Firm* — Oblon, McClelland, Maier & Neustadt, L.L.P.

(57) ABSTRACT

To provide an easy and practical iron ion removal method, as a method for purifying $P^1,P^4$-di(uridine 5'-)tetraphosphate from a solution containing iron ions.
Purification is performed by a purification method including a method for purifying $P^1,P^4$-di(uridine 5'-)tetraphosphate by removing iron ions from an aqueous solution or hydrophilic solvent solution containing $P^1,P^4$-di(uridine 5'-)tetraphosphate and iron ions, including
(1) a step of purification using a chelating resin packed column, and
(2) a step of adjusting the pH of the solution after said purification step using the chelating resin packed column to 5.5 or less, and then crystallizing $P^1,P^4$-di(uridine 5'-)tetraphosphate, or
a step of treating the solution after said purification step using the chelating resin packed column with zinc chloride-activated activated carbon.

2 Claims, 2 Drawing Sheets

METHOD FOR PURIFYING P1,P4-DI(URIDINE 5'-)TETRAPHOSPHATE

FIELD OF THE INVENTION

The present invention relates to a method for removing iron ions from an aqueous solution or hydrophilic solvent solution containing $P^1,P^4$-di(uridine 5'-)tetraphosphate and iron ions, to reduce the iron ions concentration.

BACKGROUND OF THE INVENTION $P^1,P^4$-di(uridine 5'-)tetraphosphate (hereinafter referred to as "$UP_4U$") represented by the following formula [I] or a salt thereof is used as a therapeutic agent for keratoconjunctival epithelial disorder accompanying dry eye. The compound also shows an effect of inducing expectoration, and is expected to be developed as an expectorant or a therapeutic agent for pneumonia.

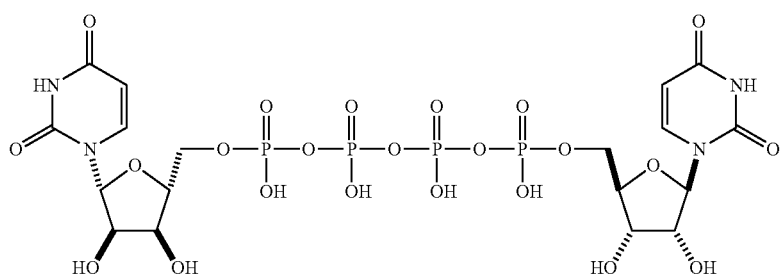

Conventionally, the following methods are known as methods for synthesizing $UP_4U$.

(1) the method by reacting uridine 5'-cyclic triphosphate prepared from dehydration condensation of uridine 5'-triphosphate (UTP), with uridine 5'-monophosphate (UMP) (Non Patent Literature 1), and the modified method thereof (Patent Literature 1).

(2) the method by activating pyrophosphoric acid with imidazole to synthesize diimidazolyl pyrophosphate, and condensing it with UMP under an anhydrous environment using an organic solvent such as dimethylformamide (DMF) (Patent Literature 2, Non Patent Literature 2).

(3) the method by reacting a phosphoric acid-activating compound represented by the following formula [II] or [III] with a phosphoric acid compound selected from the group consisting of UMP, UDP, UTP and a pyrophosphoric acid or a salt thereof (excluding UTP free) in water or a hydrophilic solvent, in the presence of a metal ion such as an iron(II) ion and an iron(III) ion (Patent Literature 3).

(In the formula [II], $R^1$ represents a uridyl group binding to the 5'-position; X represents a heterocyclic group; and n represents an integer of 1 or 2.)

(In the formula [III], X represents a heterocyclic group selected from the group consisting of an imidazolyl group, a benzimidazolyl group, and a 1,2,4-triazolyl group.)

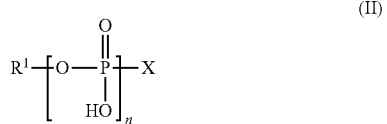

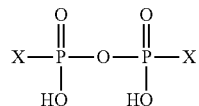

Among them, when the method (3) is employed, synthesis of $UP_4U$ with high yield, while avoiding utilization of UTP free not suitable for industrial mass production and dehydration operation of UTP salt, may be available. In addition, this method is extremely suitable for industrial large-scale synthesis of $UP_4U$ because it hardly produces by-products and can omit a complicated dehydration step according to employment of a reaction under hydrophilic conditions.

CITATION LIST

Patent Literatures

Patent Literature 1: WO 2008/012949 A
Patent Literature 2: WO 2008/024169 A
Patent Literature 3: WO 2014/103704 A
Patent Literature 4: WO 2000/020430 A

Non Patent Literatures

Non Patent Literature 1: Bioorg. & Medicinal Chemistry Letters, vol. 11, 157-160 (2001)
Non Patent Literature 2: Org. Biomol. Chem., 2011, No. 9, 730-738 (2011)

SUMMARY OF INVENTION

Technical Problem $UP_4U$ is a compound used as a raw material for pharmaceuticals, so extremely high level of impurity management is required. Therefore, it is also essential to keep the metal ions concentration at a sufficiently low degree. On the other hand, for example, in the production method (3) above, since a metal ion such as an iron(II) ion or an iron(III) ion is added to the reaction solution as a catalyst, the metal ions are contained in the $UP_4U$ solution after completion of the reaction. In such a case, it is necessary to remove the metal ions in the purification step.

Conventionally, as a purification method of $UP_4U$, a method for producing crystals of $UP_4U$ or a salt thereof has been known, wherein the method is characterized as comprising a step of purifying crude $UP_4U$ or a salt thereof via anion exchange chromatography and activated carbon chromatography, a step of adjusting the pH of the purified $UP_4U$ or its salt solution to 6 to 9 as desired, and a step of then adding a hydrophilic organic solvent at a temperature condition of 60° C. or less to thereby precipitate crystals (Patent Literature 4). However, the efficiency for the removal of metals from the $UP_4U$ solution containing iron ions has not been investigated.

On the other hand, as methods for removing iron ions contained in a solution, for example, a method of forming a precipitate derived from iron ions by using phosphoric acid or sodium hydroxide and removing the precipitate, and a method of adsorbing and removing iron ions by using a chelating resin or synthetic adsorption resin are used as ordinary methods. However, as a result of study, the present inventor has found that in the case when lowering the iron ions concentration of the $UP_4U$ reaction solution containing iron ions, the concentration of iron ions sometimes cannot be sufficiently reduced by the ordinary methods as described above depending on the condition.

Therefore, an object of the present invention is to provide a method for conveniently and practically removing iron ion as an alternative purification method of $UP_4U$.

Solution to Problem

As a result of intensive studies to solve the above problems, the present inventors have found that the iron ions in the $UP_4U$ reaction solution may be sufficiently removed and the concentration of residual iron ions can be reduced to extremely low concentration of 10 ppm or less, by removing iron ions from an aqueous solution or hydrophilic solvent solution containing $UP_4U$ and iron ions via combination between a step of column purification using a chelating resin and either a step of crystallization at pH 5.5 or less differently from the conventionally known crystallization condition, or a step of treatment using zinc chloride-activated activated carbon.

More specifically, the present invention provides the following [1] and [2].

[1] A method for purifying $P^1,P^4$-di(uridine 5'-)tetraphosphate by removing iron ions from an aqueous solution or hydrophilic solvent solution containing $P^1,P^4$-di(uridine 5'-)tetraphosphate and iron ions, including (1) a step of purification of the solution using a chelating resin packed column, and (2) a step of adjusting the pH of the solution after said purification step using the chelating resin packed column to 5.5 or less, and then crystallizing $P^1,P^4$-di(uridine 5'-)tetraphosphate, or a step of treating the solution after said purification step using the chelating resin packed column with zinc chloride-activated activated carbon.

[2] The purification method according to [1], wherein the iron ions are trivalent iron ions.

Advantageous Effects of Invention

By employing the purification method of the present invention, it is possible to produce $UP_4U$ having the same quality as $UP_4U$ produced by a method without using the catalyst, even if iron ions are used as a catalyst.

DESCRIPTION OF EMBODIMENTS

Figure 1:
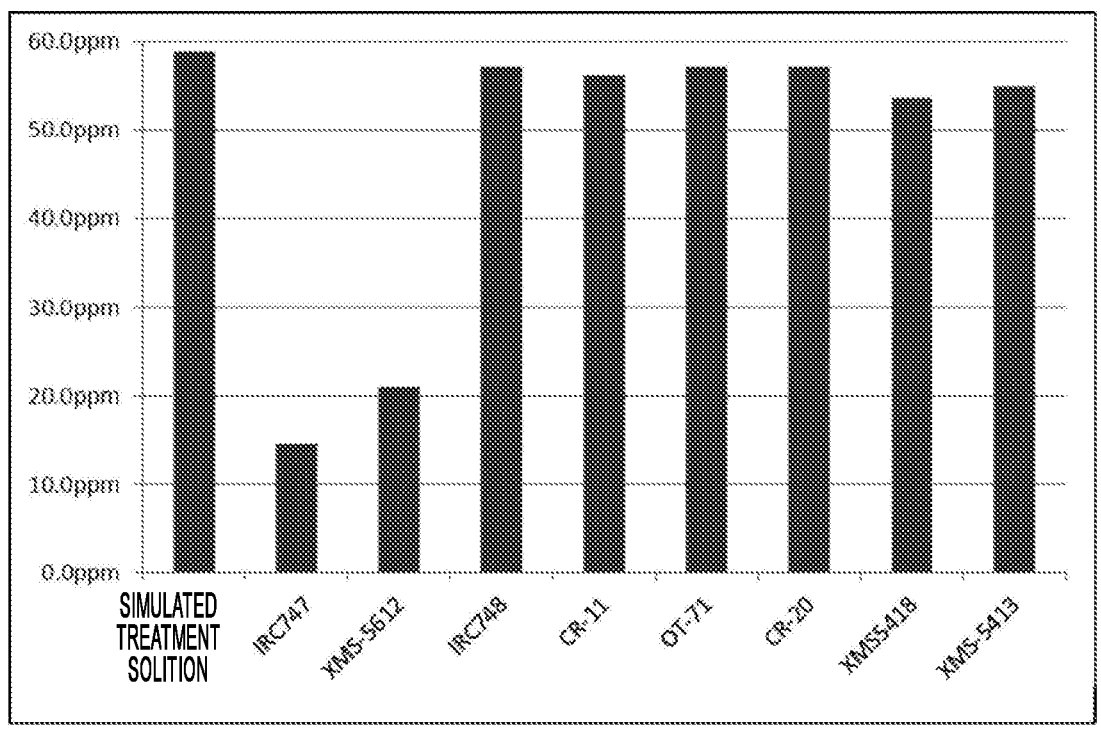
FIG. 1 shows the concentrations of iron ions relative to $UP_4U$ in solutions after chelating resin column treatment and subsequent treatment using various kinds of chelating resin column.

The method of the present invention relates to a method of removing iron ions from an aqueous solution or hydrophilic solvent solution containing $UP_4U$ and iron ions, to reduce the iron ions concentration.

The aqueous solution or hydrophilic solvent solution containing $UP_4U$ and iron ions is not limited as long as it contains $UP_4U$ and iron ions. Examples thereof include a synthetic reaction solution obtained by a production method including reacting (1) a phosphoric acid-activating compound represented by the following formula [II] or [III] with (2) a phosphoric acid compound selected from the group consisting of UMP, UDP, UTP and a pyrophosphoric acid or a salt thereof (excluding UTP free) in water or a hydrophilic organic solvent, in the presence of (3) a metal ion selected from the group consisting of an iron(II) ion and an iron(III) ion (Patent Literature 3).

(In formula [II], $R^1$ represents a uridyl group binding to the 5'-position; X represents a heterocyclic group; and n represents an integer of 1 or 2.)

(In formula [III], X represents a heterocyclic group selected from the group consisting of an imidazolyl group, a benzimidazolyl group, and a 1,2,4-triazolyl group.)

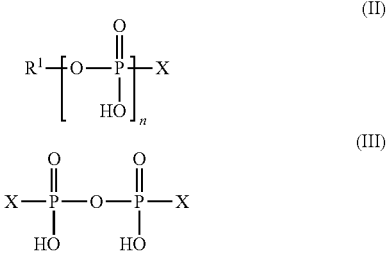

The "iron ion" of the present invention refers to an ion converted from an iron salt to a metal ion by addition thereof in water or a hydrophilic organic solvent. The kind of salt may include, for example, halide, inorganic acid salt, and organic acid salt. Further specific examples include (i) ferrous chloride, ferric chloride, and ferric bromide as examples of halides, (ii) sulfuric acid, nitric acid, and perchloric acid as examples of inorganic acid salts and (iii) organic acid salts such as trifluoromethanesulfonates, acetates, trifluoroacetates, and citrates as examples of organic acid salts. The salt may be a ferrous salt or a ferric salt, a ferric salt is preferable, and among them, ferric chloride is particularly preferable. The salt to be used may be an anhydride or a hydrate.

In the $UP_4U$ solution of the present invention, the solvent is water or a hydrophilic organic solvent. As the hydrophilic organic solvent, alcohols having 6 or less carbon atoms such as methanol and ethanol, ketones such as acetone, ethers such as dioxane, nitriles such as acetonitrile, amides such as dimethylformamide may be used.

The iron ions concentration in the $UP_4U$ solution is preferably 10 ppm or more, more preferably 60 ppm or more, and further preferably 60 ppm or more and 10% or less, with respect to $UP_4U$. Also, the $UP_4U$ concentration in the UP$_4$U solution is preferably 0.01 to 10%, more preferably 0.1 to 5%, and further preferably 1 to 3%.

The method of the present invention relates to a method for purifying UP$_4$U including, as steps for removing iron ions from the UP$_4$U solution, (1) a step of purification of the solution using a chelating resin packed column, (2) a step of performing crystallization at pH 5.5 or less, or a step of performing zinc chloride-activated activated carbon treatment.

In (1) the column purification step using the chelating resin, column purification may be performed according to an ordinary method. The kind of chelating resin to be used may include, for example, any one selected from aminophosphoric acid type, iminodiacetic acid type, polyamine type, bispicolylamine type, and isothiouronium type. Among them, aminophosphoric acid type and iminodiacetic acid type are preferable.

Commercially available products of chelating resin include IRC747 (aminophosphoric acid group Na type, manufactured by Organo Corporation), IRC748 (iminodiacetic acid group Na type, manufactured by Organo Corporation), CR-11 (iminodiacetic acid group Na type, manufactured by Mitsubishi Chemical Corporation), CR-20 (polyamine group free type, manufactured by Mitsubishi Chemical Corporation), OT-71 (iminodiacetic acid group Na type, manufactured by MUROMACHI CHEMICALS INC.), XMS-5612 (aminophosphoric acid group Na type, manufactured by MUROMACHI CHEMICALS INC.), XMS-5418 (bispicolylamine group SO$_4$ type, manufactured by MUROMACHI CHEMICALS INC.), XMS-5413 (isothiouronium group Cl type, manufactured by MUROMACHI CHEMICALS INC.).

In the step (1), specifically, an aqueous solution or a hydrophilic organic solvent solution of UP$_4$U containing iron ions is passed through a column packed with a chelating resin, and the passed solution is collected.

By the column purification step using the chelating resin, the iron ions concentration relative to UP$_4$U in the UP$_4$U solution is reduced to 60 ppm or less.

In the crystallization step (2-1) of (2), a crystallization mother liquor is first adjusted to pH 5.5 or less by adding an acid such as hydrochloric acid, phosphoric acid, sulfuric acid, nitric acid or acetic acid to the solution after the treatment (1), and subjected to crystallization. Here, pH may be 5.5 or less, and is more preferably 2.5 or more and 5.5 or less. In the crystallization, for example, the hydrophilic organic solvent is added to the UP$_4$U solution and stirred until the mixture becomes turbid, and the mixture is allowed to stand, and the precipitated crystals are collected by filtration. Examples of the hydrophilic organic solvent include alcohols having 6 or less carbon atoms such as methanol and ethanol, ketones such as acetone, ethers such as dioxane, nitriles such as acetonitrile, amides such as dimethylformamide, particularly alcohols, and preferably ethanol. In this case, in order to improve the crystallization efficiency, a seed crystal may be added simultaneously with the hydrophilic organic solvent.

In the treatment step (2-2) of (2) using zinc chloride-activated activated carbon, activated carbon treatment may be performed according to an ordinary method. In the method, zinc chloride-activated activated carbon may be added to the solution after the treatment (1) and the mixture may be stirred for about 30 minutes to 20 hours, followed by removal of the activated carbon by filtration.

The type of activated carbon used in the method of the present invention includes, for example, steam-activated and chemical-activated activated carbon, and among them, using zinc chloride-activated activated carbon is characteristic feature of the present invention. The raw material of activated carbon may be selected from, for example, wood, coconut shell, and coal. The shape may be selected from, for example, powder, crushed, granular, columnar, fibrous, and sheet-like. Commercially available products of zinc chloride-activated activated carbon include, for example, Tokusei Shirasagi M600 (manufactured by Osaka Gas Chemicals Co., Ltd.).

In the method of the present invention, (1) the column purification step using a chelating resin and (2) the crystallization step under a condition of pH 5.5 or less or the zinc chloride-activated activated carbon treatment step are performed at least once in order of (1), (2). Also, in addition to the above steps (1) and (2), the method of the present invention may further include, for example, a step of performing column purification using an ion exchange column, a step of performing other activated carbon treatment, or a step of performing crystallization again. These steps may be performed before, after, and between the steps (1) and (2).

By performing purification by the method of the present invention, the iron concentration in the UP$_4$U-containing solution can be reduced to an extremely low concentration, for example, it can be adjusted to an extremely low value of 10 ppm or less of iron content relative to UP$_4$U after the treatment.

In the method of the present invention, after purification by the zinc chloride-activated activated carbon treatment step as the step (2) is completed, UP$_4$U can be obtained with high purity by performing a crystallization treatment as necessary. As a crystallization method, for example, publicly known method (Patent Literature 4) may be used.

EXAMPLES

Reference Example

UP$_4$U was synthesized according to a known method (Patent Literature 3). Using diimidazolyl pyrophosphate as the phosphoric acid-activating compound, and UMP as the phosphoric acid compound, the condensation reaction was performed using water as a solvent and ferric chloride as a catalyst. (Formula [III], X is an imidazolyl group.)

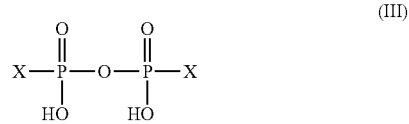

(III)

The solution after the condensation reaction was subjected to a chelating resin (IRC748, manufactured by Organo Corporation) packed column treatment. The iron ions concentration after the chelating resin treatment was 40 ppm. Thereafter, even when crystallization was performed according to a known method, the iron ions concentration did not become 40 ppm or less.

The iron ions concentration was determined following spectrometric method using 1,10-phenanthroline of JIS K 0400-57-10. Specific quantification methods are as follows.

(1) Charge a 10 mL volumetric flask with a sample and an iron standard solution (Fe100) for preparing calibration curve. Prepare a 10 mL volumetric flask that does not charge anything for blanks.

(2) Add 400 μL of a 6.0 M HCl solution and 200 μL of a 10% hydroxylamine hydrochloride solution to all volumetric flasks and sufficiently mix the mixture. Then, allow the flasks to stand for 30 minutes or more.

(3) Add 200 μL of a 0.5% o-Phenanthroline solution and 1 mL of a 50% ammonium acetate solution and make up to 10 mL.

(4) Stir well and allow the flasks to stand at room temperature for 10 minutes or more. Then, measure $OD_{510}$ of each solution.

(5) Prepare a calibration curve from the obtained $OD_{510}$ value and determine the iron ions concentration in the sample.

(Example 1) Evaluation of Combination of Chelating Resin Column Treatment and Crystallization Step As a method of adding a de-ironing treatment additionally after the chelating resin column treatment, the process for reducing the iron concentration by crystallizing the chelating treatment solution and only separating the crystal was investigated.

The evaluation was conducted by preparing a simulated treatment solution containing 38 ppm of iron relative to $UP_4U$. Specifically, 480 g of $UP_4U$ was first dissolved in deionized water and the volume of the solution was adjusted to 2 L. Then, an iron(III) chloride solution was added to the solution to adjust an iron content relative to $UP_4U$ of 38 ppm. Hydrochloric acid was added to the solution to adjust pH to be 4.5, 5.0, 5, 5, 6.0, 6.5, and 7.0, and these were used as simulated treatment solution.

200 mL of each simulated treatment solution was stirred in a 25° C. water bath, then 95% ethanol was added until the mixture became turbid (about 120 mL), seed crystals of $UP_4U$ (25 mg) were added thereto, and the mixture was stirred overnight. After confirming that crystals were sufficiently precipitated, about 40 mL of 95% ethanol was further added thereto, and the mixture was stirred. The crystals and the supernatant were separated by filtration. The obtained crystals were dissolved in 100 mL of deionized water, and the iron content was measured.

The results are shown in Table 1.

TABLE 1

| | pH | | | | | |
|---|---|---|---|---|---|---|
| | 7.0 | 6.5 | 6.0 | 5.5 | 5.0 | 4.5 |
| Fe content relative to $UP_4U$ (ppm) | 38 | 18 | 14 | 5 | 6 | 6 |

As shown in the above table, when the crystallization treatment was performed following the chelating resin treatment, the iron concentration after crystallization of the pre-crystallization solution at pH 7.0 was 38 ppm, suggesting that the iron was not removed. While, the iron concentration after crystallization when crystallized at pH 5.5 or less was 10 ppm or less, suggesting that when the crystallization was performed at a low pH condition of pH 5.5 or less, the iron concentration was able to be reduced to a very low concentration.

(Example 2) Evaluation of Combination of Chelating Resin Column Treatment and Another Treatment As a method of adding a de-ironing treatment additionally after the chelating resin column treatment, the process for reducing the iron concentration by charging an iron adsorbent (various chelating column resins or various activated carbons) to the initial chelating treatment solution was evaluated.

The evaluation was conducted by preparing a simulated treatment solution containing iron ions. Specifically, 480 g of $UP_4U$ was first dissolved in deionized water and the volume of the solution was adjusted to 2 L. Then, one obtained by adding an iron(III) chloride solution to the solution to make an iron content relative to $UP_4U$ of 60 ppm was used as a simulated treatment solution.

A simulated treatment solution adjusted to pH 2.0 was measured and charged into 14 test tubes at 4.0 mL each. Each 60 mg of chelating resin or powdered activated carbon was weighed and charged into the simulated treatment solution in the test tube, and the mixture was stirred. Twenty hours after the start of stirring, 1 mL or more of the treatment solution was sampled out and filtered with a 0.2 μm membrane filter to remove the resin and the activated carbon. The iron content was measured using 1 mL of the filtrate.

The types of chelating column resins used in the test are as follows; IRC747 (aminophosphoric acid group Na type, manufactured by Organo Corporation), IRC748 (iminodiacetic acid group Na type, manufactured by Organo Corporation), CR-11 (iminodiacetic acid group Na type, manufactured by Mitsubishi Chemical Corporation), CR-20 (polyamine group free type, manufactured by Mitsubishi Chemical Corporation), OT-71 (iminodiacetic acid group Na type, manufactured by MUROMACHI CHEMICALS INC.), XMS-5612 (aminophosphoric acid group Na type, manufactured by MUROMACHI CHEMICALS INC.), XMS-5418 (bispicolylamine group SO4 type, manufactured by MUROMACHI CHEMICALS INC.), XMS-5413 (isothiouronium group Cl type, manufactured by MUROMACHI CHEMICALS INC.).

In addition, the types of activated carbon are as follows; Shirasagi P (coconut shell/steam activation, Osaka Gas Chemical Co., Ltd.), Tokusei Shirasagi (wood/zinc chloride activation, Osaka Gas Chemical Co., Ltd.), Shirasagi A (wood/steam activation, Osaka Gas Chemical Co., Ltd.), FP-3 (material unknown/steam activation, manufactured by Osaka Gas Chemical Co., Ltd.), TAIKO K Type A (wood/activation method unknown, manufactured by Futamura Chemical Co., Ltd.).

Figure 2:
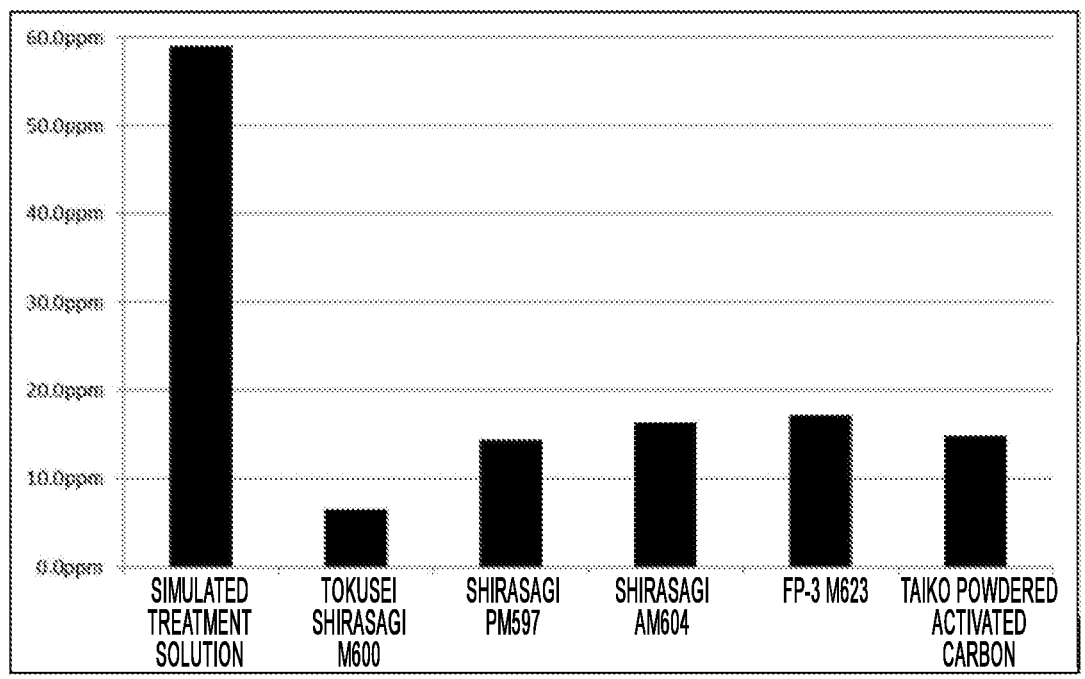
FIG. 2 shows the concentrations of iron ions relative to $UP_4U$ in solutions after chelating resin column treatment and subsequent treatment using activated carbon.

The results are shown in Tables 2 and 3 and FIGS. 1 and 2.

TABLE 2

| Resin name | Functional group | Fe concentration relative to $UP_4U$ (ppm) |
|---|---|---|
| Simulated treatment solution | — | 58.9 ppm |
| IRC747 | Aminophosphoric acid type (Na) | 14.5 ppm |
| XMS-5612 | Aminophosphoric acid type (Na) | 21.0 ppm |
| IRC748 | Iminodiacetic acid type (Na) | 57.2 ppm |
| CR-11 | Iminodiacetic acid type (Na) | 56.2 ppm |
| OT-71 | Iminodiacetic acid type (Na) | 57.2 ppm |
| CR-20 | Polyamine type (free) | 57.2 ppm |
| XMS5418 | Bispicolylamine type ($SO_4$) | 53.6 ppm |
| XMS-5413 | Isothiouronium type (Cl) | 55.0 ppm |

TABLE 3

| Activated carbon name | Material | Activation method | Fe concentration relative to UP$_4$U (ppm) |
|---|---|---|---|
| Simulated treatment solution | — | — | 58.9 ppm |
| Tokusei Shirasagi M600 | Wood | Zinc chloride | 6.5 ppm |
| Shirasagi P M597 | Coconut shell | Steam | 14.3 ppm |
| Shirasagi A M604 | Wood | Steam | 16.3 ppm |
| FP-3 M623 | Unknown | Steam | 17.1 ppm |
| TAIKO powdered activated carbon | Wood | Unknown | 14.7 ppm |

As shown in FIG. 1 above, when an additional chelating resin was added to the solution after chelating resin column treatment, iron was not removed except of using an aminophosphoric acid group Na type XMS-5612 (manufactured by MUROMACHI CHEMICALS INC.) or IRC747 (manufactured by Organo Corporation). Also, even when treated with an aminophosphoric acid group Na type resin, the iron concentration after treatment was 10 ppm or more.

While, as shown in FIG. 2, when activated carbon treatment was applied to the solution after chelating resin column treatment, the iron concentration was reduced even when any activated carbon was used. In particular, in the case of using zinc chloride-activated activated carbon, the iron concentration after treatment was less than 10 ppm, and the iron concentration was able to be reduced to a very low concentration.

The invention claimed is:

1. A method for purifying $P^1,P^4$-di(uridine 5'-)tetraphosphate by removing iron ions from an aqueous solution or hydrophilic solvent solution comprising $P^1,P^4$-di(uridine 5'-)tetraphosphate and iron ions, the method comprising:
   (1) purifying the solution with a chelating resin packed column, and
   (2) adjusting the pH of the solution after said purifying to 5.5 or less, and then crystallizing $P^1,P^4$-di(uridine 5'-)tetraphosphate, or
   treating the solution after purifying with zinc chloride-activated activated carbon.

2. The purification method of claim 1, wherein the iron ions are trivalent iron ions.

* * * * *